United States Patent [19]

Leveen et al.

[11] Patent Number: 4,968,439

[45] Date of Patent: * Nov. 6, 1990

[54] STERILIZING DEVICE AND METHOD USING POLYURETHANE IODINE SPONGE

[75] Inventors: Harry H. Leveen; Eric G. Leveen, both of Charleston, S.C.; Robert F. LeVeen, Philadelphia, Pa.

[73] Assignee: Medicinal Developments, Inc., Las Vegas, Nev.

[ * ] Notice: The portion of the term of this patent subsequent to Nov. 28, 2006 has been disclaimed.

[21] Appl. No.: 257,062

[22] Filed: Oct. 13, 1988

[51] Int. Cl.⁵ .............................................. C02F 1/68
[52] U.S. Cl. ................................. 210/764; 210/501; 210/198.1; 422/263
[58] Field of Search ...................... 210/94, 198.1, 501, 210/764; 422/263

[56] References Cited

U.S. PATENT DOCUMENTS

| | | | |
|---|---|---|---|
| 2,063,778 | 12/1936 | Andrus | 210/198.1 |
| 2,869,724 | 1/1959 | McDevitt | 210/94 |
| 4,344,930 | 8/1982 | MacRae et al. | 424/401 |
| 4,483,771 | 11/1984 | Koch | 210/501 |
| 4,529,511 | 7/1985 | Breeden et al. | 210/94 |
| 4,657,672 | 4/1987 | Allen | 210/94 |
| 4,728,498 | 3/1988 | Theevwes | 210/764 |
| 4,731,391 | 3/1988 | Garvey | 521/137 |
| 4,883,587 | 11/1989 | LeVeen et al. | 210/198.1 |
| 4,888,118 | 12/1989 | Barnes et al. | 210/198.1 |

FOREIGN PATENT DOCUMENTS 2355895 5/1974 Fed. Rep. of Germany ...... 210/501

Primary Examiner—Richard V. Fisher
Assistant Examiner—Cynthia L. Nessler
Attorney, Agent, or Firm—Gipple & Hale

[57] ABSTRACT

A canteen containing an iodine polyurethane complex open cell foam sponge for sterilization of water contained in the canteen.

13 Claims, 2 Drawing Sheets

STERILIZING DEVICE AND METHOD USING POLYURETHANE IODINE SPONGE

BACKGROUND OF INVENTION

Sterilization of water, especially in countries where sanitation is still at a primitive level, is important in the prevention of disease. Travelers are especially susceptible to the development of diarrhea. According to *Drug Therapy*, July 1988, 10 to 15 million Americans travel abroad each year, and 25% of these travelers become ill. It has been estimated that as many as 40% of patients traveling to South American countries develop diarrhea. This has been proven to be preventable by antimicrobial prophylaxis. Some physicians have prescribed antibiotics on a prophylactic basis. Therefore a simple method of sterilizing water is needed so that people can drink ordinary tap water when bottled water is not available.

Iodine is superior to chlorine, as a biocidal agent, yet chlorine is the major component used for the sterilization of water. There is less reactivity of iodine with organic matter and there is also much less microcidal variation over a wide pH range. In addition, chlorine forms chloramines in the presence of ammonia while iodine does not form iodamines. The absence of reactivity with ammonia is important in the sterilization of swimming pools where ammonia can be present in significant quantities. Two parts per million of iodine is innocuous to fishes, is harmless to the eye when introduced into the human eye, and can be ingested by mouth in large quantities without any serious sensation or discomfort. The cornea and sclera of the eye are far less sensitive to irritation by 2 to 5 parts per million of iodine in normal saline than they are to comparable germicidal concentrations of chlorine. Iodine is rapidly inactivated by the body tissues by the conversion of iodine to iodide (*Dialysis and Transplantation*, June 1979, page 590). Iodine concentrations in 2 to 5 parts per million are highly bacteriocidal and produce an imperceptible discoloration of water. The taste of the water is also not disagreeable, though there might be a slightly strange taste to the treated water. The efficacy of iodine as a sterilant for drinking water has been adequately proven in the past (*Industrial Engineering Chemistry*, 45:1009, 1953; also *Journal of the American Pharmaceutical Association*, Scientific Ed. 47:417 1958). Iodine has been shown to be superior to chlorine for the disinfection of swimming pool water (*American Journal of Public Health*, 49:1060, 1959; also *Public Health Report*, 78:393, 1963; for the comparison of iodine and chlorine as swimming pool disinfectants, see *American Journal of Public Health*, 60:535, 1970).

In a previous patent, U.S. Pat. No. 4,361,380, the present patentees describe the complexing of iodine with polyurethane and the surface liberation of iodine which would prevent pathogenic bacteria from growing on it.

SUMMARY OF THE INVENTION

The present invention describes sterilization of drinking water and disinfection of swimming pool water with a polyurethane iodine containing sponge. The sponge liberates free iodine into the receptacle containing the water by merely allowing the water to be in contact with the sponge for a short period of time. The polyurethane iodine complex slowly liberates iodine into the water in concentrations of approximately 2 to 5 parts per million, which is sufficient to kill bacteria and protozoa as well as inactivating some types of viruses. The sponge can be repeatedly used for many refills of a drinking water receptacle. In swimming pools, the water is recirculated through an iodine urethane sponge filter and the swimming pool water gradually builds up a biocidal concentration.

These and other objects and advantages of the present inventive apparatus will become more readily apparent in the following detailed description thereof together with the appended drawings;

DETAILED DESCRIPTION OF THE INVENTION

Figure 1:
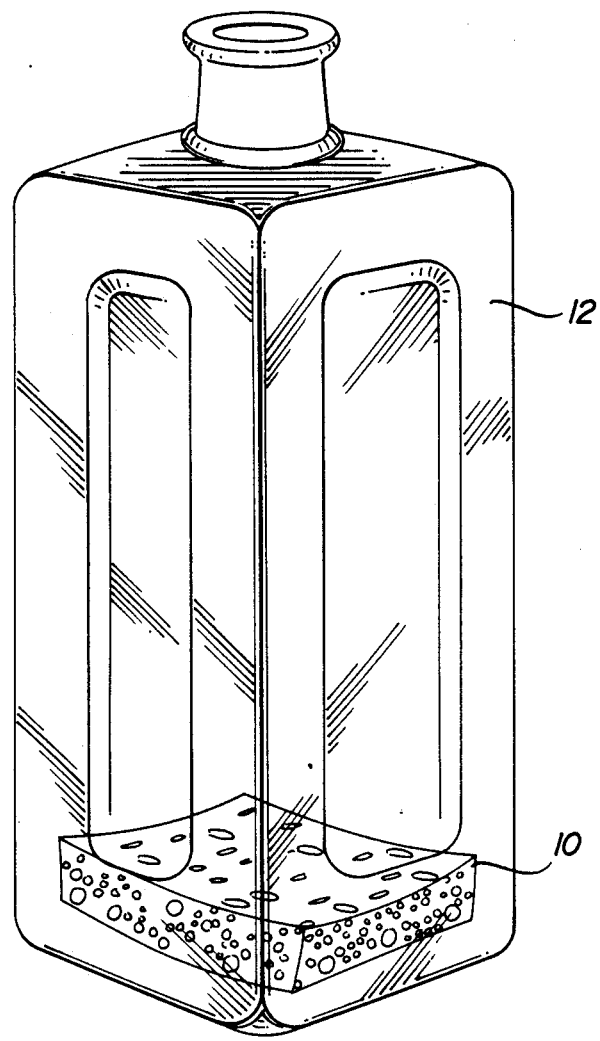
FIG. 1 is a perspective view of a canteen sterilization device with an iodine complex foam.
Figure 3:
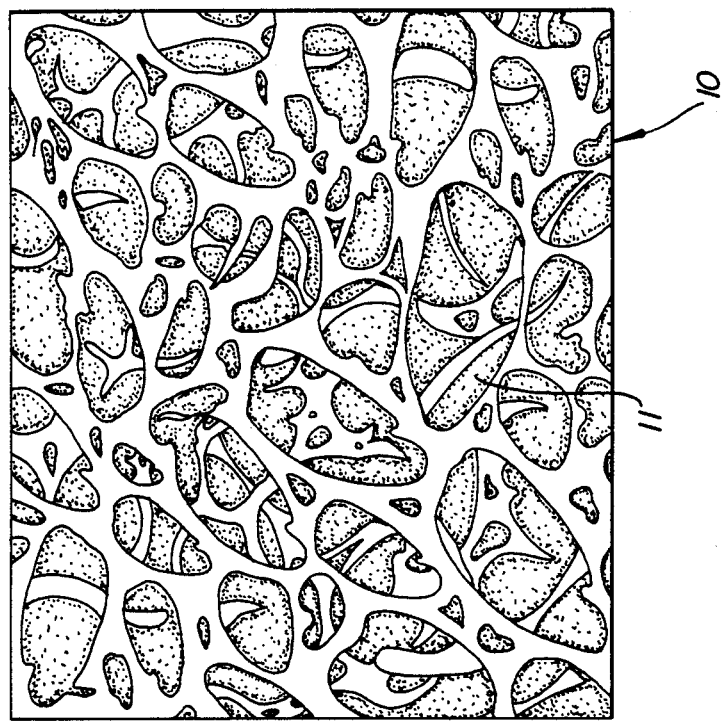
FIG. 3 is an enlarged cross-section of an open cell polyurethane sponge used in the apparatus shown in FIG. 1 and 2.
Figure 2:
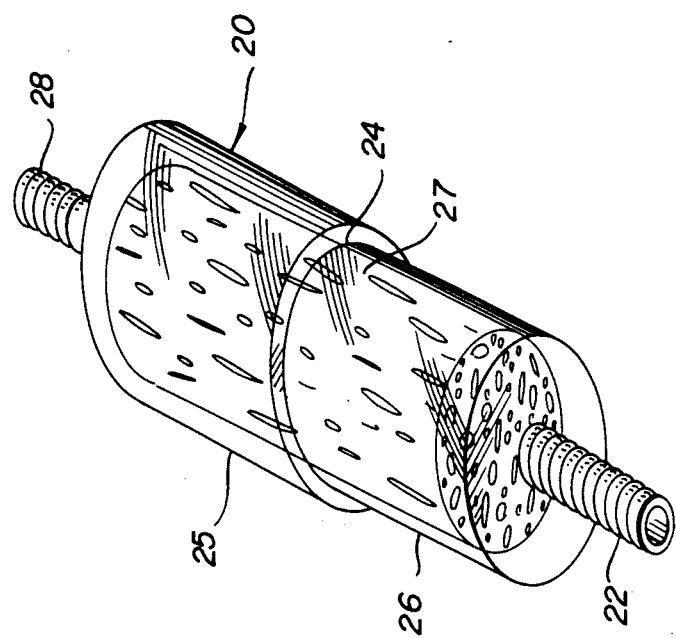
FIG. 2 is a perspective view of a filtration canister with an iodine sponge.

The preferred embodiment and best mode of the invention is shown in FIGS. 1 and 3.

The present invention uses a polyurethane sponge 10 having a large proportion of its volume as an open cell foam that can liberate sufficient iodine when equilibrium is established in a limited quantity of water to sterilize the water. The structure of the sponge can be readily seen in FIG. 3 which is a cross-section of an open cell polyurethane sponge at 5,000× magnification. In this cross-section the voids 11 are black and the polyurethane white. This makes it possible to utilize a single polyurethane iodine sponge 10 to repeatedly sterilize a canteen 12 of drinking water.

The iodine polyurethane complex dissociates slowly to release iodine until an equilibrium is established in the range from 1 to 5 parts of iodine per million of water, depending on the loading of the iodine into the polyurethane. Polyurethane sponges of either the polyether or polyester variety with a high degree of open cells containing approximately 90% open cells provide an excellent surface from which the iodine can be liberated. Such polyurethane material is standard shelf purchase material made by the Scott Company and is sold for the purpose of air filtration.

The iodine is dissolved in ethyl alcohol and the urethane sponge is treated with an iodine ethyl alcohol solution. Loading can be varied by the percentage of iodine in the iodine solution. While 5% to 10% iodine solution can be used to load the sponge, a 7% iodine solution will produce a satisfactory concentration in the polyurethane sponge, staining the sponge a deep brown color. When the sponge is washed in water, there is little or no leaching of the iodine so that the solution leaving the sponge is relatively colorless. The sponge is washed until the excess iodine has been released. All uncombined iodine can be totally washed from the sponge with a 10% sodium or potassium iodide solution. It should be noted that iodide does not complex with the polyurethane and possesses no bacteriocidal power. Therefore, the loading of the polyurethane must be accomplished, not with potassium or sodium iodide, but with a solution of elemental iodine. While various sized sponges ranging from 2 to 8 cubic centimeters have been used with canteen 12, a 5 cubic centimeter sponge placed in a one quart clear plastic canteen containing water will sterilize the water in the canteen in less than 2 hours. As the sponge weakens in its release of iodine, longer time periods are needed, and an equilibrium is achieved at 5 parts per million of iodine in the solution in a freshly treated sponge. As the iodine leaches out of the sponge, the sponge will gradually become discolored, and when the color is a light tan color, it should be discarded and a new sponge utilized to sterilize the water. Therefore the color of the iodine itself acts as an indicator of when the sponge has become inactive. Since only 5 parts iodine in a million are liberated into the water, only 5 micrograms of iodine are utilized by one quart of water. A sponge containing only a quarter of a gram of iodine would be capable of sterilizing 50,000 quarts of water. Obviously, a properly treated sponge in a small container would last almost indefinitely. Such a sponge placed in canteens would prevent infection in military troops, travelers, and users of swimming pools, and would protect the public from disease as a public health measure.

It is also possible to sterilize a swimming pool by repeatedly pumping the water through an open cell polyurethane iodine filter apparatus 20. With swimming pools, the sponge 27 would be utilized as a filter through which the swimming pool water would circulate. Thus water would be pumped through inlet conduit 22 into a clear plastic canister 24 holding an iodine polyurethane sponge 27 which fills the interior of the canister 24 forming a filter through which the water flows. The treated water passes from sponge 27 out of the canister 24 through outlet 28 into the swimming pool. The canister 24 is preferably formed of two cylindrical portions 25 and 26 which are threaded to receive one another so that the portions can be threadably mated to form a water tight container and allow easy access to the sponge 27 for removal and cleaning and/or replacement of a new sponge. Pump means not shown but well known in the art, pumps water through the inlet conduit and recirculates the water from the swimming pool. Obviously, for satisfactory sterilization, it would be necessary for the swimming pool water to filter the contents of the swimming pool repeatedly. Though the initial time utilized to sterile the swimming pool would be longer with the large capacity of the swimming pool, once equilibrium has been reached, it would not require rapid turnover to keep the water sterile.

Polyurethane iodine sponges also have therapeutic applications in the treatment of some types of infection. For instance, povone iodine has been used in the treatment of various types of vaginitis. However, this material is a brownish material which stains and must be administered in a liquid form or with sponges saturated with povone iodine. Povone iodine has been successfully used for yeast infections, bacterial infections, and protozoan infections of the vaginal tract. An iodine polyurethane sponge would serve as well without the necessity for staining liquid solutions. It may also be used as a prophylactic for disease prevention. The use of an iodine polyurethane sponge can substitute for the use of povone iodine anywhere in the body for therapeutic applications.

While a presently preferred form of the present invention has been set forth here and above, it is to be understood that the invention is not limited thereby. In particular, the steps of the inventive process are interchangeable, may be interchanged and are equivalent. It is to be understood that the specific details shown are merely illustrative and that the invention may be carried out in other ways without departing from the true spirit and scope of the following claims.

What is claimed is:

1. A canteen receptacle, an iodine polyurethane complex sponge in the form of an open cell foam containing at least 90% open cells treated with elemental iodine placed within said canteen receptacle, said treated sponge liberating iodine into the water in a concentration ranging from 1 to 5 parts per million for repeated sterilization of water contained in said canteen receptacle.

2. A receptacle as claimed in claim 1 wherein said canteen is metal and said sponge has a size ranging from 4 to 6 cubic centimeters.

3. A receptacle as claimed in claim 1 wherein said open cell foam is a polyurethane sponge of the polyether variety.

4. A receptacle as claimed in claim 1 wherein said open cell foam is a polyurethane sponge of the polyester variety.

5. A receptacle as claimed in claim 1 wherein said canteen is a plastic container with a capacity to hold a quart of water and said sponge has a size ranging from 4 to 6 cubic centimeters.

6. A receptacle as claimed in claim 5 wherein said plastic is clear.

7. A canteen for sterilization of water comprising a canteen vessel having a liquid capacity of about one quart and a iodine treated polyurethane sponge sized from 4 to 6 cubic centimeters positioned within said canteen vessel, said sponge containing iodine which is liberated into water placed in said canteen vessel in a concentration ranging from 1 to 5 parts per million which is suitable to kill bacteria and protoza in repeated filling of said canteen.

8. A canteen as claimed in claim 7 wherein said canteen vessel is constructed of clear plastic.

9. A canteen as claimed in claim 7 wherein said polyurethane sponge is polyether.

10. A canteen as claimed in claim 13 wherein said polyurethane sponge is polyester.

11. A method for sterilization of unsterilized water using an open cell sponge provided with an iodine concentration comprising:
(a) dissolving elemental iodine in an ethyl alcohol to obtain an elemental iodine solution ranging from 5 to 10% iodine;
(b) treating the open cell sponge with the iodine ethyl alcohol solution;
(c) producing a suitable concentration of iodine in the sponge sufficient to liberate iodine into water in concentration ranging from 1 to 5 parts per million sufficient to kill bacteria and protozoa; and
(d) placing the sponge in a receptacle for contact with unsterilized water containing bacteria and protozoa.

12. A method as claimed in claim 11 including an additional step after step c of washing the sponge having a concentration of iodine with a sodium iodide solution.

13. A method as claimed in claim 11 including an additional step after step c of washing the sponge having a concentration of iodine with a potassium iodide solution.

* * * * *